US012188038B2

(12) United States Patent
Tran et al.

(10) Patent No.: US 12,188,038 B2
(45) Date of Patent: Jan. 7, 2025

(54) METHODS, DEVICES AND SYSTEMS FOR ENHANCED TRANSDUCTION EFFICIENCY

(71) Applicants: Emory University, Atlanta, GA (US); Georgia Tech Research Corporation, Atlanta, GA (US); Children's Healthcare of Atlanta, Inc., Atlanta, GA (US)

(72) Inventors: Reginald Tran, Atlanta, GA (US); Wilbur Lam, Atlanta, GA (US); David Myers, Atlanta, GA (US); Christopher Doering, Atlanta, GA (US); Harold Spencer, Marietta, GA (US)

(73) Assignees: Emory University, Atlanta, GA (US); Children's Healthcare of Atlanta, Inc., Atlanta, GA (US); Georgia Tech Research Corporation, Atlanta, GA (US)

( * ) Notice: Subject to any disclaimer, the term of this patent is extended or adjusted under 35 U.S.C. 154(b) by 978 days.

(21) Appl. No.: 16/696,456

(22) Filed: Nov. 26, 2019

(65) Prior Publication Data
US 2020/0095608 A1 Mar. 26, 2020

Related U.S. Application Data

(63) Continuation of application No. 15/369,598, filed on Dec. 5, 2016, now abandoned.

(60) Provisional application No. 62/263,137, filed on Dec. 4, 2015.

(51) Int. Cl.
 *C12N 15/86* (2006.01)
 *C12N 15/87* (2006.01)
(52) U.S. Cl.
 CPC .......... *C12N 15/86* (2013.01); *C12N 15/87* (2013.01)
(58) Field of Classification Search
 None
 See application file for complete search history.

(56) References Cited

U.S. PATENT DOCUMENTS

| | | | |
|---|---|---|---|
| 4,220,725 A | 9/1980 | Knazek et al. | |
| 5,498,537 A | 3/1996 | Bresler et al. | |
| 6,403,369 B1 * | 6/2002 | Wood .................... | C12M 23/04 435/288.1 |
| 8,815,597 B2 | 8/2014 | Chono et al. | |
| 2004/0072278 A1 | 4/2004 | Chou et al. | |
| 2004/0203147 A1 | 10/2004 | Triffitt et al. | |
| 2007/0111296 A1 | 5/2007 | Mn et al. | |
| 2008/0176318 A1 | 7/2008 | Wilson et al. | |
| 2008/0219959 A1 | 9/2008 | Carbone et al. | |
| 2008/0220522 A1 | 9/2008 | Antwiler | |
| 2008/0227190 A1 * | 9/2008 | Antwiler ............... | C12M 29/18 435/297.5 |
| 2008/0274091 A1 * | 11/2008 | Slepushkin ............. | A61P 37/00 435/457 |
| 2009/0250130 A1 * | 10/2009 | Studer ................. | B81C 1/00119 264/494 |
| 2010/0120077 A1 * | 5/2010 | Daridon ............. | G01N 33/4833 435/288.5 |
| 2012/0135446 A1 | 5/2012 | Collins et al. | |
| 2013/0029875 A1 | 1/2013 | Stehno-Bittel et al. | |
| 2015/0037890 A1 * | 2/2015 | Mershin ................ | C12M 35/08 435/285.1 |

FOREIGN PATENT DOCUMENTS

| | | | | |
|---|---|---|---|---|
| WO | WO-2006113727 A2 * | 10/2006 | ........ | B01L 3/502746 |
| WO | 2008023771 A1 | 2/2008 | | |
| WO | 2009072003 A2 | 6/2009 | | |
| WO | 2013072288 A1 | 5/2013 | | |
| WO | 2016073602 A2 | 5/2016 | | |
| WO | 2016118780 A1 | 7/2016 | | |

OTHER PUBLICATIONS

Luni et al. Stochastic Model-Assisted Development of Efficient Low-Dose Viral Transduction in Microfluidics. Biophysical Journal, 2013. 104: 934-942.*
Cao et al. "A 3D microfluidic device fabrication method using thermopress bonding with multiple layers of polystyrene film." Journal of Micromechanics and Microengineering, 2015; 25:065005 (1-10).
Chuck et al. "Membrane Adsorption Characteristics Determine the Kinetics of Flow-Through Transductions." Biotechnology and Bioengineering, 1996; 51:260-270.
Dodo et al. "An Efficient Large-Scale Retroviral Transduction Method Involving Preloading the Vector into a RetroNectin-Coated Bag with Low-Temperature Shaking." Plos One, 2014; 9(1): e86275 (1-12).
Johnson et al. "Integration of Multiple Components in Polystyrene-based Microfluidic Devices Part 1: Fabrication and Characterization." Analyst, 2013; 138(1):129-136.
Kim et al. "Microfluidic approaches for gene delivery and gene therapy." Lab Chip, 2011; 11:3941-3948.
Saint-Gobain "Customer Solutions Example"—"Cell Harvest" Brochure. [retrieved from the Internet <URL:https://www. celltherapy. saint-gobain.com/sites/imdf.biotech.com/files/cell-harvest-flyer. pdf> on Feb. 13, 2017].
Tran et al. "Simplified prototyping of perfusable polystyrene microfluidics." Biomicrofluidics, 2014; 8:046501-1-046501-10.

(Continued)

*Primary Examiner* — Allison M Fox
*Assistant Examiner* — Kimberly A Aron
(74) *Attorney, Agent, or Firm* — Emory Patent Group

(57) ABSTRACT

The systems and methods are directed to leveraging the channel geometry and configuration to overcome diffusion limitations of current transduction systems. The methods may include a method of transducing target cells using a device. The device may include at least one continuous channel. The method may include delivering target cells and viral vectors into a transduction region of the channel. After transducing for some incubation time, a flushing solution may be delivered. The method may include collecting transduced cells after the transducing incubation time and the delivering of the flushing solution.

20 Claims, 6 Drawing Sheets

(56) References Cited

OTHER PUBLICATIONS

Non-Final Office Action issued on Aug. 15, 2018 in U.S. Appl. No. 15/369,598.
Final Office Action issued on May 31, 2019 in U.S. Appl. No. 15/369,598.

* cited by examiner (i) (ii) (iii) (iv)

(i) (ii) (iii) (iv)

(v)

METHODS, DEVICES AND SYSTEMS FOR ENHANCED TRANSDUCTION EFFICIENCY

CROSS-REFERENCE TO RELATED APPLICATIONS

This application is a continuation of U.S. patent application Ser. No. 15/369,598 filed Dec. 5, 2016, which claims the benefit of U.S. Provisional Application No. 62/263,137 filed Dec. 4, 2015. The entirety of each of these applications is hereby incorporated by reference for all purposes.

BACKGROUND

Through decades of research and innovation, viruses that once plagued humanity with sickness and disease have been transformed into tools with the potential to provide a permanent cure for various genetic disorders and cancers. In recent years, researchers and clinicians have achieved success in treating a variety of diseases using viral vectors to achieve transduction. However, currently utilized methods and platforms for cell culture and transduction can be inefficient. Current platforms can also require a substantial amount of viral vectors, due to the diffusion limitations that result in a substantial amount of viral particles decaying before they can reach the cells. One solution has been to use greater quantities of the virus but that can be both cost-prohibitive (e.g., due to current production processes) and potentially toxic to the target cells.

SUMMARY

Thus, there is need for a more efficient systems, devices and methods that can achieve therapeutic levels of transduction using less amount of the virus.

In some embodiments, the methods may include a method of transducing target cells with a viral vector using a device. The device may include at least one continuous channel. The method may include delivering target cells and viral vectors into a transduction region of the channel through a first inlet/outlet simultaneously and/or consecutively when one or more additional inlets/outlets that are located in a region of the channel downstream of the transduction region are closed. After transducing for some incubation time, a flushing solution may be delivered through one or more of the additional inlets/outlets. The method may include collecting transduced cells after the transducing incubation time and the delivering of the flushing solution.

In some embodiments, the devices may include a device or a platform configured to transduce target cells with a viral vector. In some embodiments, the device may include a flushing region; and a connection region disposed between the transduction region and the flushing region. The transduction region, the flushing region, and the connection region may form or define a continuous channel. The device may further include one or more inlets/outlets disposed at end of the transduction region and one or more inlets/outlets disposed on the flushing region. The channel may have a height and a width greater than the height.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
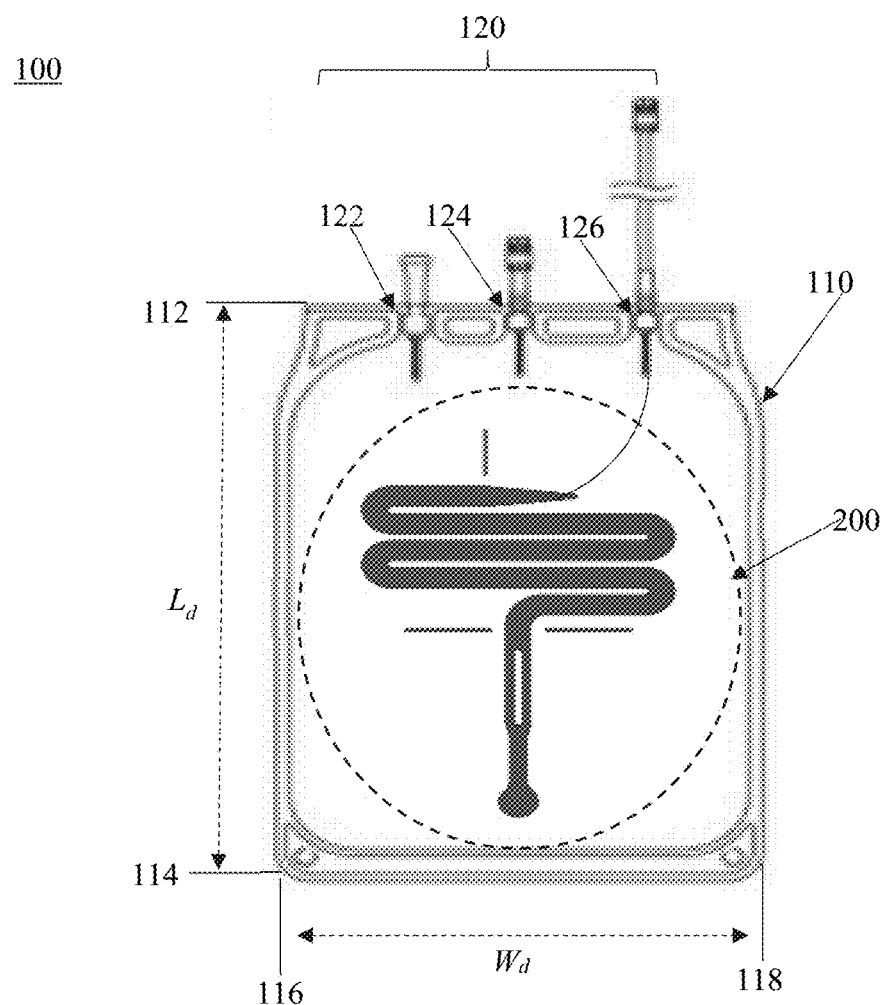
FIG. 1 shows an example of a device according to some embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems, methods, and devices according to the disclosure can dramatically increase the transduction efficiency by increasing the contact between the vectors and target cells, for example, before the degradation of the vectors (e.g., viral vector). By enabling large quantities of cells to be exposed to sufficient vector concentrations, transduction times can be reduced while minimizing vector waste. Therefore, the systems, methods, and devices according to the disclosure can reduce the total amounts of the vector used to achieve sufficient vector concentrations can also be reduced overcome issues related to the various sources of variability in vector titration and inconsistent infectivity between various cell types. Thus, the systems, methods, and devices according to the disclosure can achieve transduction at a reduced cost as compared to conventional transduction systems.

As used herein, the term "vector" means the combination of any carrier and any foreign gene(s). The vector may include non-viral vectors, viral vectors, among others, and any combination thereof. For example, non-viral vectors may include but are not limited to liposomes, spheroplasts, red blood cell ghosts, colloidal metals, calcium phosphate, DEAE Dextran plasmids, among others, or a combination thereof. The viral vectors may include but are not limited to retroviral vectors, lentiviral vectors, pseudotype vectors, adenoviral vectors, adeno-associated viral vectors, among others, and any combination thereof.

In some embodiments, the systems, devices, methods can be configured for fluid-based transduction protocols. For example, the protocols may include static (e.g., single loading), flow transduction (i.e., continuous loading), among others, or a combination thereof. Static transduction and flow transduction protocols according to some embodiments are discussed in more detail below.

In some embodiments, the device can be configured for ex-vivo, static and/or flow transduction. In some embodiments, the device may be in a form of an encased cultured plate device, a bag-like device, a flask-like device among others, or a combination thereof. In some embodiments, the device may include one or more closed fluid channels.

As used herein, the term "communicate" (e.g., a first component "communicates with" or "is in communication with" a second component) and grammatical variations thereof are used herein to indicate a fluidic relationship between two or more components and/or channel segments. As such, the fact that one component/channel segment is said to communicate with a second component/channel segment is not intended to exclude the possibility that additional components may be present between, and/or operatively associated or engaged with, the first and second components.

Figure 2A:
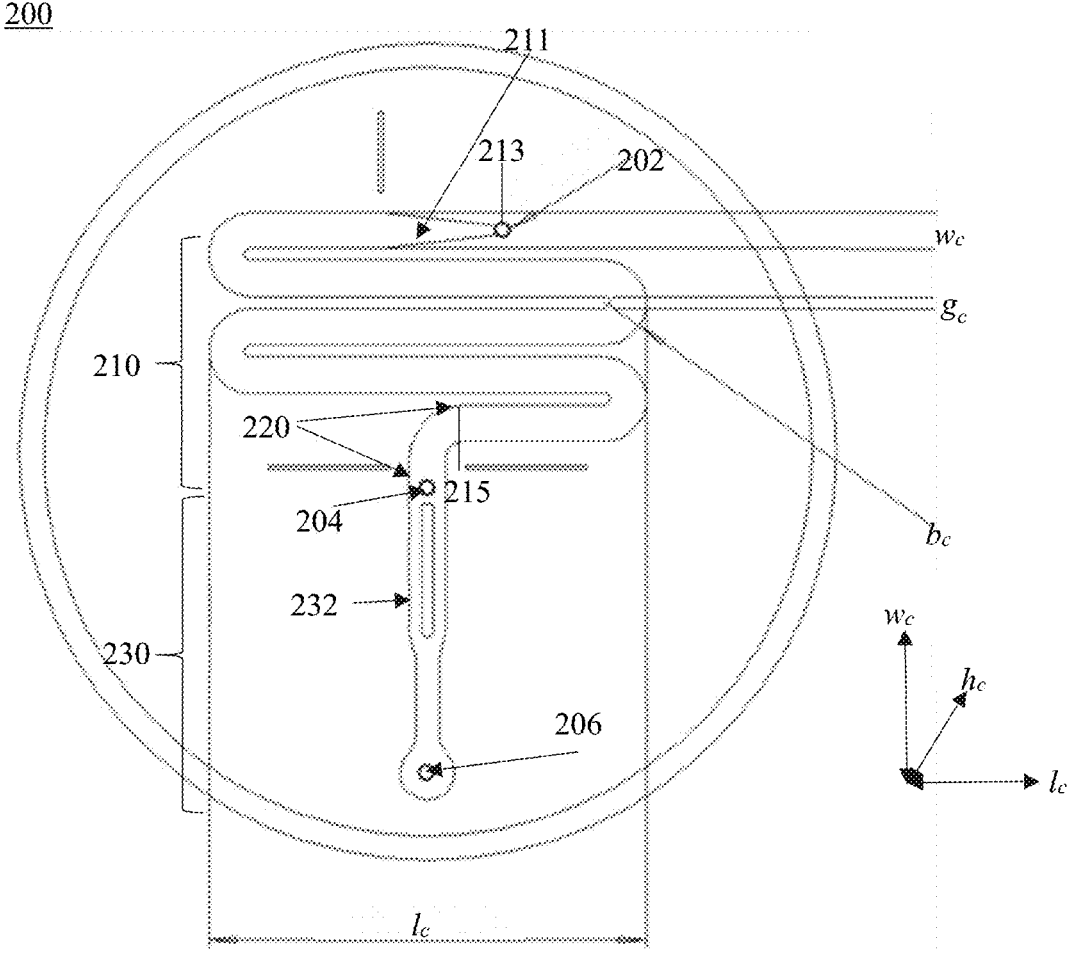
FIG. 2A shows an enlarged view of the cell processing device shown in FIG. 1 and FIGS. 2B and 2C show additional enlarged views of the cell processing device shown in FIGS. 1 and 2A.
Figure 2B:
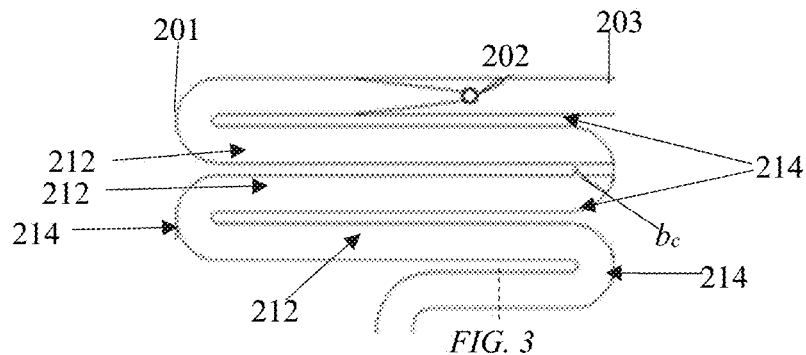
Figure 2C:
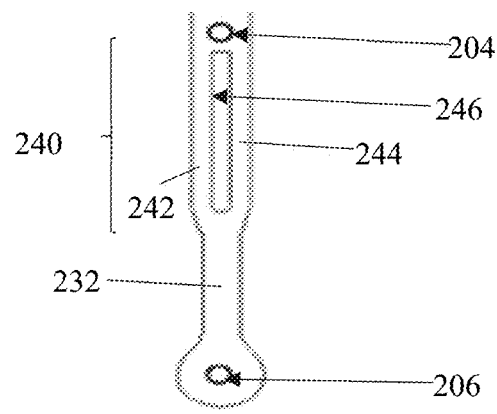

FIGS. 1 and 2 show an exemplary device 100 according to some embodiments. As shown in FIG. 1, the device 100 may have a body 110. The body 110 may have a first end 112, an opposing second end 114, and a length ($L_d$) therebetween. The body 110 may also have a first side 116 and an opposing, second side 118 and a width ($W_d$) therebetween. In some embodiments, the length and the width of the body 110 may be different. For example, as shown in FIG. 1, the length may be longer than the width of the body 110. In some embodiments, the length and the width may be the same.

In some embodiments, the device 100 may include a cell processing section 200 disposed within the body. In some embodiments, the cell processing section 200 may include a plurality of fluid channels. In some embodiments, the cell processing section 200 may include one or more regions of one or more fluid channels (referred to as "one or more regions") that are in fluid communication with each other.

In some embodiments, the one or more regions may include: (i) one or more transduction/transfection regions 210 (later referred to as "transduction regions"); (ii) one or more flushing regions 230 that are in fluid communication with the one or more transduction/transfection regions; (iii) additional region(s); and/or (iv) any combination thereof. The transduction region(s) 210 can correspond to region(s) of the channel in which transduction/transfection can be performed and the flushing region(s) 230 can correspond to region(s) of the channel in which the stagnant fluid during the cell removal/collection can be addressed (e.g., by flushing). In some embodiments, the one or more transduction/transfection regions 210 and the one or more flushing regions 230 may each be connected by a connection region 220.

In some embodiments, the transduction region 210, the connection region 220, and the flushing region 230 together can form a continuous channel. In some embodiments, the device 100 may include one or more inlets/outlets disposed along the channel. The device 100 may include one or more of the following: 1) a loading inlet; 2) a collection outlet for the cells; 3) a flushing inlet; 4) a collection outlet for the excess cells/vectors (also referred to as "excess collection outlet"); 5) among others; 6) or any combination thereof. In some embodiments, the device 100 may include at least two inlets/outlets: 1) a first inlet/outlet configured to be loading inlet and a collection outlet (also referred to as "loading inlet/collection outlet"); and 2) a second inlet/outlet configured to be a flushing inlet and/or excess collection outlet (also referred to as "flushing inlet/outlet"). For example, the device 100 may include at least a first inlet/outlet disposed along transduction region(s) 210 and one or more additional (second) inlets/outlets disposed along the connection region(s) 220 and/or the flushing region(s) 230. In some embodiments, the first inlet/outlet may be configured to be a loading inlet and collection outlet and the additional inlet/outlet may be configured to be a flushing inlet and/or excess collection outlet. The device 100 may include any number of inlets/outlets.

In some embodiments, at least the transduction region(s) 210 can be configured so that the cells form a monolayer for a homogenous virus exposure. In some embodiments, the channels disposed in the transduction region (s) 210 can also be configured to provide a high surface area-to-volume ratio that can overcome diffusion limitations of conventional systems.

In some embodiments, each transduction region 210 may include a plurality of channel segments 212 and a plurality of junction segments 214. The plurality of junction segments 214 may be disposed between and fluidly connect two of the channel segments 212

In some embodiments, the channel segments 212 and junction segments 214 may be disposed in a pattern. In some embodiments, each channel segment 212 may be disposed to extend along the width or the length of the body 110. In the example shown in FIG. 1, each channel segments 212 may be disposed to extend along the width of the body 110 between the first side 116 and the second side 118. In other embodiments, each channel segment 212 may be disposed to extend along the length of the body 110 between the first end 112 and the second end 114.

In some embodiments, each channel segment 212 may be a straight segment that extends between sides/ends of the body 110 having a length ($l_c$) as shown in FIGS. 1-2b. As shown in the figures, the length ($l_c$) of each channel segment 212 can extends parallel to the width ($W_d$) of the device body 110 but will understood that the length ($l_c$) of each channel segment 212 may extend parallel to the length ($L_d$) of the body 110.

In the other embodiments, the one or more segments 212 may have a different shape. For example, the one more segments 212 may have a curved shape. In some embodiments, the one or more segments 212 may each have the same shape, for example, as shown in FIG. 1. In other embodiments, the one or more segments 212 have different shape.

In some embodiments, each junction segment 214 may have a curved shape (e.g., rounded bend), for example, as shown in FIGS. 1-2b. For example, the each junction segment 214 may have an angle bend ($b_c$) and a channel gap ($g_c$). As shown in the figures, the angle bend may be about 180°. In other embodiments, the one or more junction segments 214 may have the same and/or different shape, angle bend, channel gap, or any combination thereof. For example, one or more junction segments 214 may have an angled, square-like shape.

In some embodiments, the transduction region 210 may include any number of channel segments 212 and junction segments 214. By way of example, the transduction region 210 may include more or less channel segments 212 and junction segments 214 shown in the figures.

In some embodiments, the device 100 may include an inlet/outlet 202 disposed along transduction region(s) 210 and one or more additional inlets/outlets disposed along the connection region(s) 220 and/or the flushing region(s) 230. In some embodiments, the first inlet/outlet may be configured to be a loading/seeding inlet and collection outlet and the additional inlets/outlets may be configured to be a flushing inlet and excess collection outlet.

As shown in the figures, the device 100 may include an inlet/outlet 202 disposed at a first end 213 of the transduction region 210 and an inlet/outlet 204 between the connection region 220 and/or the flushing region 230. For example, the inlet/outlet 202 may be an inlet through which the cells and virus, simultaneously and/or sequentially, can be loaded into the processing portion 200; the cells can be collected/removed from the channel after completing the transduction protocol; among others; or any combination thereof. For example, the inlet/outlet 204 may be (1) an inlet through which flushing fluid can be loaded and/or (2) an outlet through which excess cells and/or vectors that have been flushed away during transduction can be collected/removed (e.g., excess collection outlet).

In some embodiments, a portion of the channel segment 212 (channel portion 211) disposed adjacent to the inlet/outlet 202 may be tapered. The tapering of that portion 211 can prevent trapping of the cells within that portion and direct the cells toward the inlet/outlet 202 for collection.

In some embodiments, the channel segments 212 may be disposed in a pattern so as not to extend past the same points with respect to the body 110. For example, each of the channel segments 212 may be disposed so as extend between the same points disposed with respect to the width/length of the device 110. In this way, most of the channel segments 212 may be substantially the same length. Although the segment 211 including the inlet/outlet 202 is shown to be smaller in length (starts at a point between junction segments), that segment 211 may be disposed to start at a point close to the junction segment 214 so that can be substantially the same length as the other segments 212. In other embodiments, the channel segments 212 may be disposed so as to be offset (i.e., to extend between different points with respect to the body 110).

In some embodiments, the flushing region 230 may include one or more channel segments 232. The flushing region 230 may be fluidly connected to the transduction region 210 by the connection region 220 disposed between second end 215 and the flushing region 230. As shown in the figures, the flushing region 230 may be fluidly connected to the transduction region 210 by the connection region 220. In some embodiments, the connection region 220 may have a bend angle of 90°. In other embodiments, the connection region 220 may have a different bend angle, shape, among other, or a combination thereof.

In some embodiments, the device 100 may include additional ports disposed on the channel segments of the flushing region 230. For example, the device 100 may include an inlet/outlet 206. The inlet/outlet 206 may be configured to be a secondary flushing inlet/outlet. For example, the inlet/outlet 206 may be an outlet through which the cells and/or vectors remaining after the first flush and collection (via inlet/outlet 204) during transduction can be collected/removed.

As shown in the figures, the segment 232 extends between the inlet/outlets 204 and 206. It however will be understood that the inlet/outlet 204 and/or 206 may be omitted. Additionally, the segment 232 may include one or more additional inlets/outlets.

In some embodiments, as shown in the figures, the channel segment 232 of the flushing region 230 may be a straight segment that is disposed on the device 110 so as to extend perpendicular to the channel segments 212 of the transduction region 210. In some embodiments, the channel segment 232 may be disposed so as to extend between the inlets/outlets 204 and 206.

In some embodiments, the channel segment 232 may be disposed in different configurations with respect to the connection region 220 and/or the transduction region 210. For example, the channel segment 232 may be disposed parallel to channel segment 212.

In some embodiments, the device 100 may include one or more flushing regions disposed at different locations with respect to the device body 110 in addition to or in alternative to the region 230 shown in FIGS. 1-2B. For example, the one or more flushing regions may be disposed adjacent on either side of the transduction region 210 so as to extend adjacent to the junction segments 214, be disposed within the transduction region, for example, between the channel segments 212 and junction segments 214, among others, or a combination thereof.

In some embodiments, the channel segment 232 may include one or more split portions 240 in which the segment 232 is separated by one or more splitting member 246 so that the channel segment 232 divides or splits into multiple channels. As shown in the Figure, the segment 232 may separate into two separate channels 242 and 244 along the portion 240.

In some embodiments, the flushing region(s) 230 may include additional dividing members along the length of the channel segment, additional dividing members 246 along the length and/or within a dividing portion, among others, or any combination thereof. By including the transfusion region 230 with split portion(s) 240, fluid can better align along the sides so that flushing of the cells from the channel can be maximized.

As shown in the figures, the transduction region 210, the connection region 220 and the flushing region 230 together can form a continuous channel disposed between two inlet/outlet ports in the device 100. As shown in the figures, the transduction region 210, the connection region 220, and the flushing region 230 together can form a continuous channel disposed between the inlets/outlets 202 and 206 in the device 100. In the figures, the connection region 220, and the flushing region 230 can be considered to be downstream of the transduction region 210. The inlet/outlet 202 can be considered the loading inlet and the inlets/outlets 204 and 206 can therefore be considered to be disposed on the channel downstream of the inlet/outlet 202.

In some embodiments, the device 100 may include more than one continuous channel disposed between inlets/outlets of the device 100. For example, the device 100 may include additional continuous channel(s) disposed between inlets/ outlets having additional transduction region(s), connection region(s), and flushing region(s).

In some embodiments, the device 100 may include any number of transduction regions 210, connection regions 220, and flushing regions 230. Although the device 100 is shown as having one transduction region 210, one connection region 220, and one flushing region 230, it will be understood that the device may include more than one transduction region 210, connection region 220, and flushing region 230. For example, the device may include an additional flushing region 230 and connection region 220 disposed adjacent to and/or within the transduction region 210.

Figure 3:
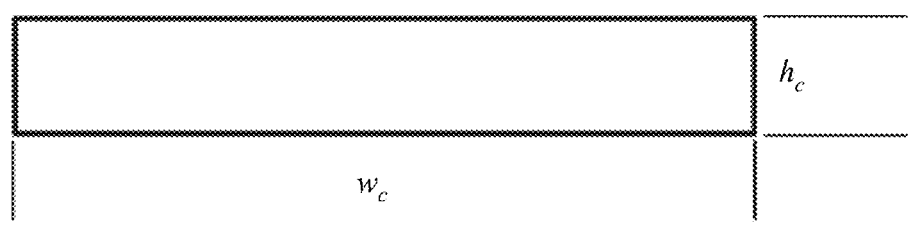
FIG. 3 shows a cross-sectional view of a channel shown in FIG. 2B according to some embodiments.

FIG. 3 shows an example of a cross-section of the continuous channel disposed in the processing section 200 (i.e., the continuous channel that extends through the transduction, connection, and flushing regions). It will be understood that the cross-section does not correspond to the split portion 240 but the entire split portion 240 (e.g., 242, 244 and 246) may have the same dimensions of the cross-section. In some embodiments, the continuous channel disposed in the processing section 200 may have a height $h_c$ that is within the range of about 50-100 μm and/or a width $w_c$ that is within the range of about 3000-5000 μm. In some embodiments, the height and/or width may be greater than those ranges, less than those ranges, among others, or a combination thereof.

In some embodiments, for processing a cell number of about 1,000,000-4,000,000, the channel may have aspect ratios between height to width between 1:10 and 1:90. In some embodiments, the channel may have a height between about 50-250 μm. The width may be between 20-90× greater than the height. For example, the width may be between about 1000-5000 μm. In some embodiments, the total surface area of the transduction region may be between about 9.5-15 cm$^2$.

In some embodiments, for processing a cell number of $10^7$-$10^8$ cells, the channel may have aspect ratios between height to width between 1:10 and 1:100. In some embodiments, the channel may have a height between about 50-250 μm. The width may be between 20-100× greater than the height. In some embodiments, total surface area of the transduction region may be between 50-500 cm$^2$. In some embodiments, the total surface area for processing $10^7$ cells should be about 50 cm$^2$ for processing $10^8$ cells should be about 500 cm$^2$.

The channel geometry/dimensions can depend on material and manufacturing process. For example, the height of the channel may be smaller than 150 μm (e.g., about 96 μm) if manufactured using Photolithography, and larger than 200 μm (e.g., about 210 μm) if manufactured using CNC Milling. The channel dimensions/geometry of the channel according to embodiments provide a more efficient transduction. More specifically, the channel dimensions/geometry can address the issues with loading the cells/vectors due to the large surface area and aspect ratio of the channels by properly constraining the fluid in the channels. To have a large surface area, narrow channels need to be longer in length, which can significantly increase fluidic resistance thereby impeding cell loading. Conversely, shorter wide channels can be prone to collapsing due to extremely high aspect ratio, thereby requiring internal supports that can increase fabrication complexity for methods, such as xurography and disturb flow patterns for non-static transductions, thereby reducing cell recovery. Furthermore, air pockets can easily form in large channels that would make uniform loading difficult.

Figure 4A:
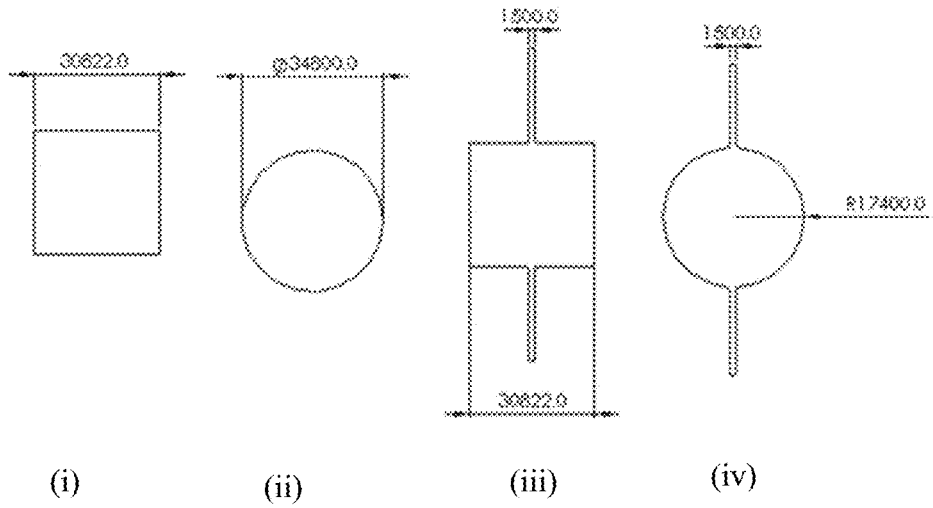
FIG. 4A shows examples (i)-(iv) of different channel geometries.
Figure 4B:
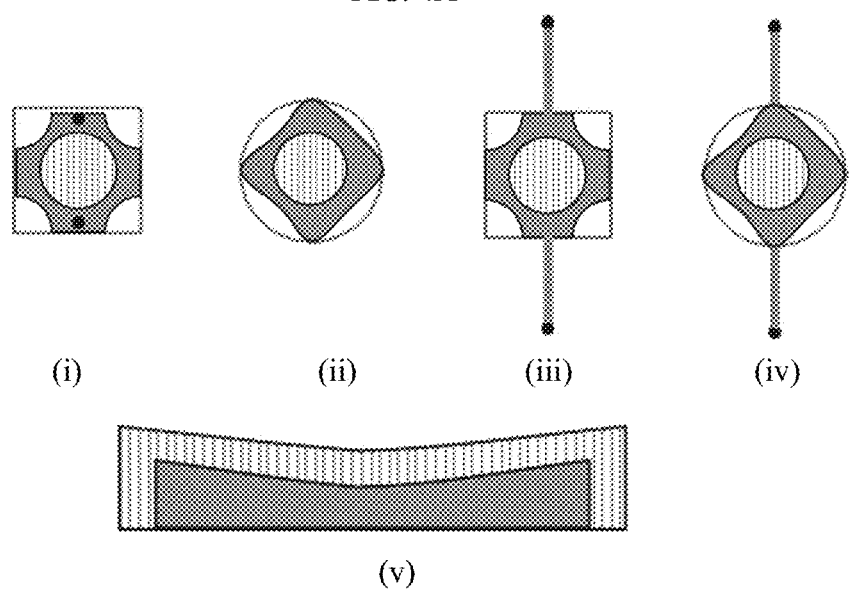
FIG. 4B show examples (i)-(iv) of failures of the different channel geometries (i)-(iv) shown in FIG. 4A and example (v) of a cross-sectional view of failed channel geometries, for example, shown in examples FIG. 4 B (i) and (iii)
Figure 4C:
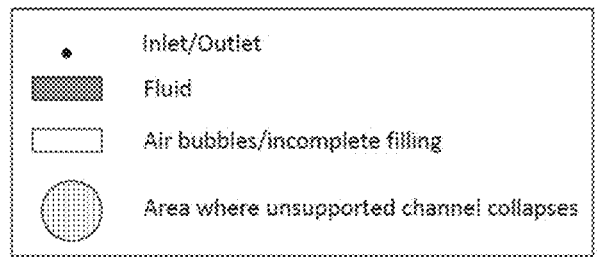
FIG. 4C shows a legend for examples (i)-(v) shown in FIG. 4B.

FIGS. 4A and 4B show examples of failed channel geometry. FIG. 4A shows channel designs (i)-(iv) having the same height but with varying widths. Channel design 4A (iv) has the same width as 4(A) (ii). As shown in FIG. 4B (i)-(iv), these designs generally fail because they collapse and incomplete fill due to having such a high aspect ratio. For example, FIG. 4B (iii) shows a failure example showing areas where the loading might not be uniform due to air bubbles and the center would collapse due to the high aspect ratio and FIG. 4B (v) is an example of the cross-section of examples 4A/B (i) and (iii) or of a general channel collapse in which the top surface will either sag slightly or make contact with the bottom surface. FIG. 4C shows a legend for FIGS. 4(B) (i)-(v).

Figure 5:
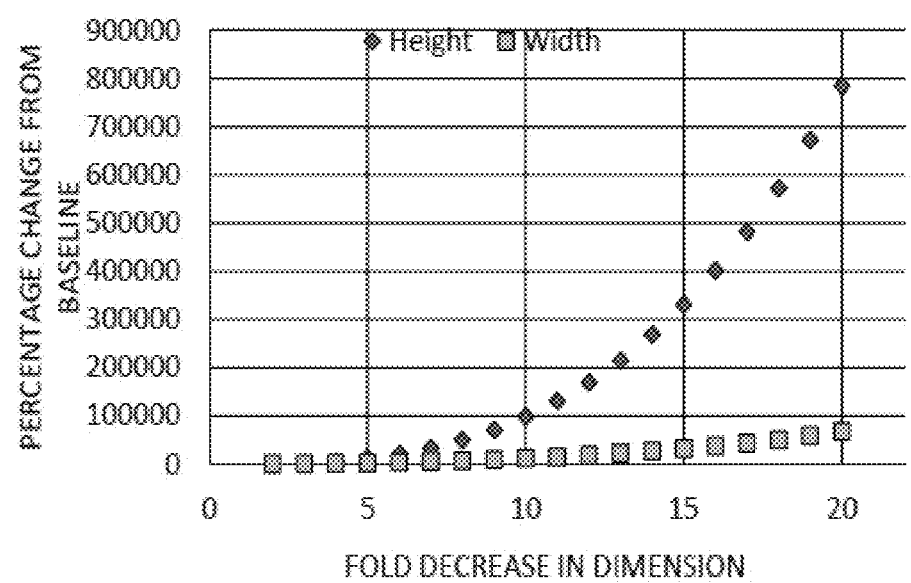
FIG. 5 is a graph that shows how fluidic resistance is increased from a baseline for fold decreases in either channel height (diamonds) or channel width (squares)

FIG. 5 shows a graph of fluidic resistance using hypothetical, different channel designs having different heights and widths. The hypothetical baseline design had a 3000 um in width and 1000 um in height. This graph shows how the fluidic resistance can increase with respect to the baseline (the large open minimalistic "channels") for fold differences in either height or channel width. For example, a 10-fold decrease in height increases the fluidic resistance nearly 8-fold from baseline compared to if the width was decreased by 10-fold from baseline. Therefore, to address the potential fluidic resistance in the channel, the width of the channel should be proportionally greater than height.

In some embodiments, the device 100 may include a coating entirely or partially along the channel within the processing section 200. For example, the coating may a removable cell adhesive. The coating may include but is not limited to RetroNectin®, other polymers such as poly-L-lysine, cell adhesives such as CellTak, among others, or any combination thereof. In some embodiments, the coating may be disposed along the channel within the transduction region 210. In other embodiments, the coating may also be disposed along the channel disposed within the connection region 220 and/or the flushing region 230.

In some embodiments, the device 100 may include one or more access ports 120 disposed on the body 110 that fluidly communicate with the one or more inlets/outlets (e.g., 202, 204, 206) and channel regions (e.g., 210, 220, 230) of the device 100 and that can be configured to connect or communicate with one or more external systems/devices (e.g., to perform the transduction using the device 100). In some embodiments, the device may include an access port for each inlet/outlet.

In some embodiments, the access ports 120 may be disposed on one or more side of the device 100. As shown in FIG. 1, the access ports 120 may be disposed along first end 112. In some embodiments, the access ports 120 may be disposed on other side of the device 100. In some embodiments, the access ports 120 may be disposed on a different end/side of the device 100. For example, the access ports 120 may be disposed on the device to correspond to the location of the inlets/outlets (e.g., 202, 204, and 206).

In some embodiments, one or more access ports 120 may include an adapter configured to connect that access port and inlet/outlet to an external system/device, tubing, etc. The adapter may include a luer lock device, a Barbed device, septum seal device, among others, or any combination thereof. In some embodiments, the one or more adapters and/or access ports may be integrated into the device 100, for example, if the device has a bag-like form.

In some embodiments, the one or more access ports 120 may include access port 122 disposed to communicate with the inlet/outlet 202, an access port 124 disposed to communicate with the inlet/outlet 204, and access port 126 disposed to communicate with the inlet/outlet 206.

In some embodiments, the one or more access ports 120 and/or the inlets/outlets 202, 204, and/or 206 may be in a closed position as the default configuration. The one or more access ports 120 and/or the inlets/outlets 202, 204, 206 may be configured to open (e.g., using an adapter and/or other mechanism) to allow fluid through when one or more external devices are attached. For example, the device 100 may include a septum seal at the access ports and/or the inlets/outlets 202, 204, and 206.

In some embodiments, the one or more access ports 120 and/or the inlet/outlets 202, 204, and/or 206 may be in an open position as the default configuration. In some embodiments, the device 100 may include one or more locking members (e.g., stoppers) to close those ports and/or inlets/outlets.

As mentioned above, the device 100 may be in a form of an encased plate device, a bag-like device, a flask-like device among others, or a combination thereof. The device 100 may be manufactured of a sterilizable material using any known manufacturing processes. The sterilizable material may include but is not limited to silicone elastomer (e.g., polydimethylsiloxane (PDMS)), thermoplastics (e.g., such as polystyrene and polymethylmethacrylate), polystyrene, silicon, or glass. For example, for an encased plate device, the device may be manufactured using photolithographic methods, molding methods (e.g., using curing on a master mold, which can be manufactured, for example, using computer numerical controlled (CNC) micro-milling), xurography, among others, or a combination thereof. For example, for the bag-like device, the channels may be formed using hot embossing process, xurography, injection molding, among others, or a combination thereof.

In some embodiments, the device 100 may be configured to be used with any known devices and/or systems capable of performing static and flow transduction protocols. For example, the systems may be an automated or semi-automated system capable of performing cell isolation, expansion, transduction, among others, or a combination thereof. The systems may include any apheresis machines and/or systems. The systems may include but are not limited to CliniMACS Prodigy or CliniMACS Plus (Miltenyi Biotec), COBE cell processor (Terumo BCT) Xuri cell expansion system (GE Healthcare), among others, or any combination thereof.

In some embodiments, the device 100 may be configured to be used with systems and/or devices under a static transduction and/or flow transduction protocol. Static transduction protocol may refer to any protocol in which the target cells and virus are single loaded. Flow transduction protocol may refer to any protocol in which the virus are continuously perfused after the cells are loaded into the device and can be immobilized in the coating provided on the device and/or reagent added to the device before loading (e.g., RetroNectin®). For example, flow transduction protocols may include but are not limited to constant perfusion, recirculating perfusion, and/or low-dose consecutive perfusions, among others, or a combination thereof. For example, for a constant perfusion protocol, after the cells can be substantially immobilized within the transduction region, viral vectors may be constantly perfused through device for entire transduction duration. For a recirculating perfusion protocol, for example, after the cells can be substantially immobilized within the transduction region viral vectors may be recirculated through the device, for example, using a peristaltic pump.

For example, for low dose consecutive perfusion, after the cells can be substantially immobilized within the transduction region, viral vectors can be loaded and allowed to incubate under static conditions. After a shortened transduction time where most of the virus should have adsorbed onto the cells, a fresh stock of viral vectors can be loaded into the device to replenish the cells with virus and media. This can be done as many times as necessary to achieve the desired virus exposure or transduction time. By performing the consecutive transductions in static, potential issues of heterogeneity can be avoided It is also understood that the devices according to be embodiments can exist alone or may be a part of a system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current and the like; systems capable of performing transduction/transfection protocols (including those provided above); among others; or any combination thereof.

Figure 6:
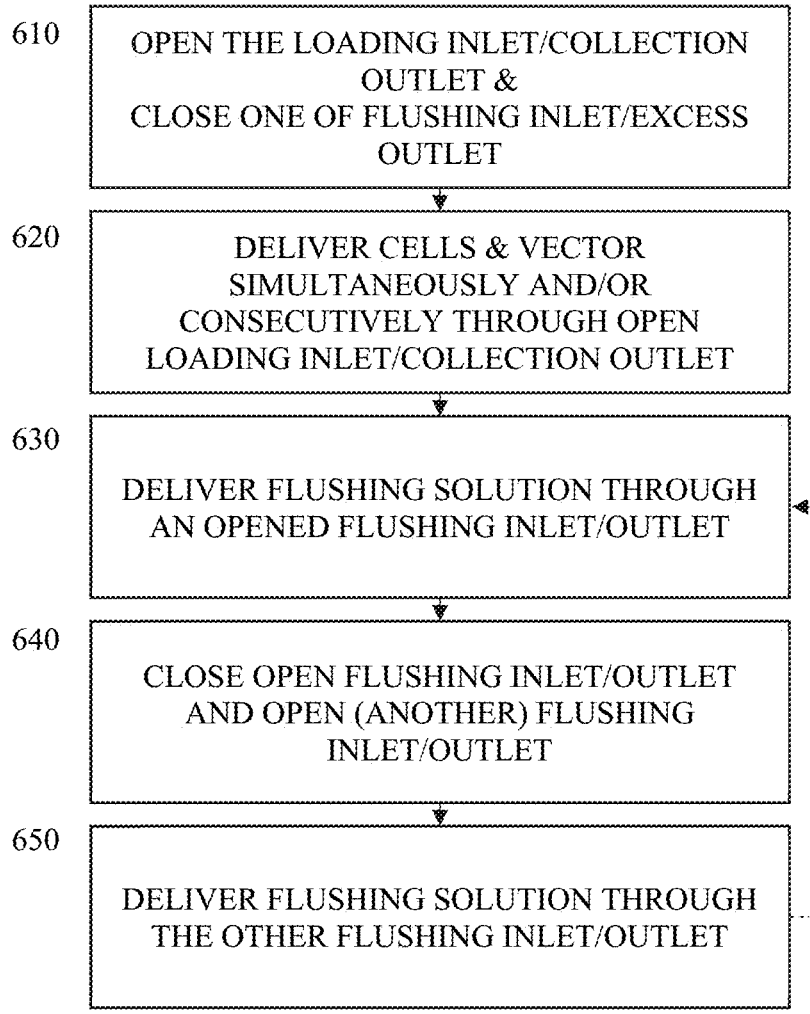
FIG. 6 shows a method of transducing target cells with a viral vector using a device according to embodiments.

FIG. 6 shows an exemplary method 600 of using a device according to embodiments to transduce cells. In some embodiments, the method 600 may be performed automatically and/or semi-automatically by one or more external device and/or system and/or manually using external devices and/or systems. The methods are described with respect to the device 100 but will be understood that the method may be performed using devices according to other embodiments.

In some embodiments, the method 600 may include a step 610 of (1) opening at least the first inlet/outlet disposed at the first end of the transduction region 210 and (2) closing a flushing inlet/excess collection outlet disposed downstream. By way of example, if the device includes more than 2 flushing inlets/excess collection outlets, the step 610 may including 1) opening, if necessary, the loading inlet/collection outlet (202) and at least one of the flushing inlets/excess collection outlets downstream (204) and 2) closing one or more of the flushing inlet/excess outlets downstream from the opened flushing inlet(s)/excess collection outlet(s) (e.g., inlet/outlet 206).

After the inlets/outlets (e.g., 202 and 204) are open for fluid communication and one or more downstream flushing inlet(s)/excess collection outlet(s) are closed, the method 600 may include step 620 of loading the target cells and viral vectors through the first inlet/outlet (e.g., 202) according to the transduction protocol. For example, for static transduction, the target cells and viral vectors may be simultaneously loaded into the device 100 through the first inlet/outlet (e.g., 202) using a device (e.g., syringe, pump etc.) for static transduction protocols. For example, for flow transduction protocols, the target cells may be loaded into the channel (e.g., transduction region 210) through the first inlet/outlet (e.g., 202) and incubated within the device 100 for a period for time so that the target cells are immobilized in the channel (e.g., immobilized by the coating agent (RetroNectin®)). After the incubation period, the viral vectors may be loaded into the channel (e.g., transduction region 210) through the first inlet/outlet (e.g., 202) by a device (e.g., syringe, pump, etc.) using the flow transduction protocol (e.g., constant, recirculating, low dose consecutive transduction, among others, or any combination thereof). During the loading step, the one of the flushing inlet/excess collection outlet (e.g., 204) can collect the excess cells and/or viral vectors that move past the transduction region 210.

Next, after the viral vectors and target cells are loaded into the device 100 for the desired transduction time in an incubator, the method 600 may include a step 630 of delivering a flushing solution using a device (e.g., syringe and/or pump) through one or more of the opened flushing inlet/excess collection outlet (e.g., 204). The flushing solution may be any solution, for example, a buffer solution such as Phosphate-buffered saline (PBS). The flushing solution can cause the cells to move to first inlet/outlet (202) for collection. Before this step, a collection chamber (e.g., collection bag) may be connected to the inlet/outlet 202 to collect the cells that are flushed.

After the device 100 is flushed with a flushing solution via each opened flushing inlet/excess collection outlet (e.g., 204), the method 600 may include a step 640 of closing one or more of the opened flushing inlets/excess collection outlets (e.g., 204) and opening one or more flushing inlets/excess collection outlets (206) that are downstream of the flushing inlet(s)/excess collection outlet(s) (204) used in steps 610-630. The one or more flushing inlets/excess collection outlets may be different and/or the same from those opened in step 610.

After which, the method 600 may include a step 650 of delivering a flushing solution through one or more of the opened flushing inlets/excess collection outlets (e.g., 206). The flushing solution may be the same solution (e.g., PBS) as step 530 or a different solution. Due to the one or more split portions 240 of the segment 232 in the flushing region 230 and the laminar flow imposed by the channel dimensions, the fluid flushed through the inlet/outlet 206 can be directed along the sides of the channel (left and right walls from the top view displayed in all drawings) at these slower/stagnant fluid regions to maximize cell recovery after transduction.

In some embodiments, steps 630-650 may be repeated, for example, for when the device includes additional flushing inlet(s)/outlet(s) and/or flushing regions 230. In some embodiments, the method 600 may also performed each processing section disposed on the device.

It will be understood that the transduced cells can be collected via inlet/outlet 202 after steps 520-550 (i.e., after the cells and viral vectors are loaded into the device for the desired transduction time).

The above method may be modified based on the default configuration of the device. For example, if the one or more of the inlets/outlets are in a closed position, as a default, than the steps associated with closing those inlets/outlets may be omitted. Alternatively, if one or more of the inlets/outlets are in an open position, as a default, than the steps associated with opening those inlets/outlets may be omitted.

The disclosed devices and transduction methods can enable significant reduction in viral vector requirements by leveraging the channel geometry to overcome diffusion limitations of current systems. Moreover, the high surface area-to-volume ratio of the channel geometry can efficiently bring the viral vector into cell contact before degradation occurs, thereby reducing transduction times while minimizing viral vector waste and total amounts used by enabling large quantities of cells to be exposed to sufficient vector concentrations.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method of cell transduction, comprising:
   simultaneously introducing a load of target cells and viral vectors into a channel of a device;
   incubating the device for a period of time to transduce the target cells;
   flowing a flushing solution through the channel to cause transduced cells to move toward an inlet/outlet of the device; and
   collecting the transduced cells from the inlet/outlet;
   wherein the channel has a cross-section, the cross-section having a height and a width, the width of the channel being greater than the height; and
   wherein the height is about 50-250 μm.

2. The method according to claim 1, further comprising:
   connecting a collection chamber to the inlet/outlet before the flowing the flushing solution to collect the transduced cells during the collecting;
   wherein the load of target cells and viral vectors are simultaneously introduced into the inlet/outlet.

3. The method according to claim 1, wherein the channel has a total surface area of about 9.5 cm$^2$-500 cm$^2$.

4. The method according to claim 3, wherein the width is at least 3000 μm and the ratio between the height and the width is about 1:10 and 1:100.

5. The method according to claim 1, wherein an amount of the target cells delivered into the channel are at least 10$^6$.

6. The method according to claim 1, wherein the introducing the target cells into the channel forms a monolayer of the target cells for homogenous exposure to the viral vectors.

7. The method according to claim 1, wherein the channel includes a cell adhesive coating and the channel includes one or more regions, at least one region including a plurality of channel segments and at least one junction segment that is disposed between and fluidly connecting two channel segments of the plurality of channel segments.

8. A method of transducing target cells, comprising:
   simultaneously introducing a load of target cells and viral vectors into a channel of a device so that the target cells form a monolayer, the channel including a cell adhesive coating;
   incubating the device for a period of time to transduce the target cells;
   flowing a flushing solution through the channel to cause transduced cells to move toward an inlet/outlet of the device; and
   collecting the transduced cells from the inlet/outlet;
   wherein the channel has a cross-section, the cross-section having a height and a width, the width of the channel being greater than the height; and
   wherein the height is about 50-250 μm and the channel has a total surface area of at least 9.5 cm$^2$.

9. The method according to claim 8, wherein an amount of the target cells delivered into the at least one channel is at least 10$^6$.

10. The method according to claim 8, wherein the width being at least twenty times greater than the height.

11. The method according to claim 10, wherein the width is at least 3000 μm and the channel includes one or more regions, at least one region including a plurality of channel segments and at least one junction segment that is disposed between and fluidly connecting two channel segments of the plurality of channel segments.

12. The method according to claim 8, further comprising:
connecting a collection chamber to the inlet/outlet before the flowing to collect the transduced cells during the collecting;
wherein the load of target cells and viral vectors are simultaneously introduced into the inlet/outlet.

13. The method according to claim 8, wherein the viral vectors are introduced using a flow transduction protocol.

14. The method according to claim 8, wherein the ratio between the height and the width is about 1:10 and 1:100.

15. A method of transducing target cells, comprising:
simultaneously introducing a load of target cells and viral vectors into a channel of a device through a first inlet/outlet, the target cells including at least $10^6$ cells;
incubating the device for a period of time to transduce the target cells;
flowing a flushing solution through the channel to cause transduced cells to move toward the first inlet/outlet or a second inlet/outlet of the device; and
collecting the transduced cells from the first inlet/outlet or the second inlet/outlet;
wherein the channel between the first inlet/outlet and the second inlet/outlet has a cross-section, the cross-section having a height and a width, the width of the channel being greater than the height; and
wherein the height is about 50-250 μm and the channel has a total surface area of at least 9.5 $cm^2$.

16. The method according to claim 15, wherein the width being at least twenty times greater than the height.

17. The method according to claim 15, wherein the width is at least 3000 μm and the channel includes one or more regions, at least one region including a plurality of channel segments and at least one junction segment that is disposed between and fluidly connecting two channel segments of the plurality of the channel segments.

18. The method according to claim 15, further comprising:
connecting a collection chamber to the first inlet/outlet or the second inlet/outlet before the flowing the flushing solution to collect the transduced cells during the collecting;
wherein the load of target cells and viral vectors are simultaneously introduced into the first inlet/outlet.

19. The method according to claim 15, wherein the introducing the target cells into the channel forms a monolayer of the target cells for homogenous exposure to the viral vectors.

20. The method according to claim 15, wherein the ratio between the height and the width is about 1:10 and 1:100.

* * * * *